United States Patent [19]
Schulman et al.

[11] Patent Number: 5,531,679
[45] Date of Patent: Jul. 2, 1996

[54] FLUIDIC INFUSION SYSTEM FOR CATHETER OR PROBE

[76] Inventors: Joseph H. Schulman, 10650 Comet Way, Santa Clarita, Calif. 91351; Orville R. Rule, III, 2572 Basil La., Los Angeles, Calif. 90077

[21] Appl. No.: 212,226

[22] Filed: Mar. 14, 1994

[51] Int. Cl.[6] .................................................. A61M 31/00
[52] U.S. Cl. ........................... 604/65; 604/131; 604/247; 604/264; 604/280; 128/DIG. 12
[58] Field of Search .................................... 607/120–122; 604/171, 264, 67, 83, 96, 102, 114, 891.1; 128/12, 13

[56] References Cited

U.S. PATENT DOCUMENTS

| | | |
|---|---|---|
| 3,995,617 | 12/1976 | Watkins et al. . |
| 4,360,031 | 11/1982 | White . |
| 4,485,813 | 12/1984 | Anderson et al. . |
| 4,522,195 | 6/1985 | Schiff . |
| 4,563,170 | 1/1986 | Aigner . |
| 4,694,838 | 9/1987 | Wijayarthna et al. . |
| 4,800,898 | 1/1989 | Hess et al. . |
| 4,819,662 | 4/1989 | Heil, Jr. et al. . |
| 4,844,099 | 7/1989 | Skalsky et al. . |
| 4,934,369 | 6/1990 | Maxwell .................................. 128/637 |
| 4,954,129 | 9/1990 | Giuliani et al. ......................... 604/264 |
| 5,090,422 | 2/1992 | Dahl et al. . |
| 5,154,165 | 10/1992 | Elliott et al. . |
| 5,207,655 | 5/1993 | Sheridan . |
| 5,220,917 | 6/1993 | Cammilli et al. . |
| 5,282,844 | 2/1994 | Stoker et al. . |
| 5,304,219 | 4/1994 | Chernoff et al. . |
| 5,322,500 | 6/1994 | Johnson et al. . |
| 5,344,439 | 9/1994 | Otten . |

*Primary Examiner*—C. Fred Rosenbaum
*Assistant Examiner*—Perry E. Van Over
*Attorney, Agent, or Firm*—Fitch, Even, Tabin & Flannery

[57] ABSTRACT

A fluidic infusion system introduces a select liquid chemical into the environment surrounding the functional end of an in vivo catheter or probe. The catheter/probe typically has a sensor or electrode positioned near or at its closed distal end. A plurality of spaced radial openings are formed in an appropriate pattern adjacent to the end of the catheter/probe for introducing the select liquid chemical into the appropriate environment. The catheter/probe has at least one lumen extending through its length for directing the liquid chemical from a controlled pump to the radial openings. The openings are positioned within the catheter/probe so that when the catheter/probe is inserted into the appropriate environment, e.g., within a blood stream inside an artery or vein, the openings are upstream from the sensor or electrode relative to the flow of blood within such environment, thereby allowing the natural flow of blood to carry the liquid chemical from the radial openings to the sensor or probe area, where it can perform its intended function. The openings allow fluid flow therethrough only in one direction—from the lumen to the environment surrounding the catheter/probe. The catheter/probe may include a plurality of lumens for transporting differing liquid chemicals to the concerned environment.

25 Claims, 7 Drawing Sheets

FLUIDIC INFUSION SYSTEM FOR CATHETER OR PROBE

BACKGROUND OF THE INVENTION

The present invention relates to medical catheters or probes which are placed within living tissue relative to the vascular or neurological anatomy of a patient (which may be a human or an animal) to perform a measurement, sensing or stimulation function. More particularly, the invention provides a system for introducing a select fluid, e.g., a liquid chemical, into the environment of the functional end of the catheter or probe. The liquid chemical may be selected to prevent, or reduce, formation of thrombus, tissue growth and encapsulation of the invasive portion of the catheter, to medicate and prevent infection at the site of implantation, to anesthetize surrounding neurostructure or to apply a calibration or control substance into the investigated environment.

Catheters and probes are utilized for numerous measurement, sensing, and stimulation functions of body fluids and tissues, typically through an invasive procedure in which the catheter or probe is inserted within a vascular member, e.g., a vein or artery, through which the investigated fluid flows or implanted within the investigated tissue. The catheter or probe usually is constructed to form a lumen through which a sensor or electrode and its conducting element is passed to the site of interest and terminates with the sensor or electrode protruding from its end to gain exposure to the investigated fluid or tissue. For example, an in vivo sensor for measuring pH, glucose or oxygen content in blood may be delivered to the select site through a catheter inserted in an artery leading to the site. Alternatively, an electrode for stimulating muscle tissue may be brought to the site of excitation through a tubulus probe implanted in adjacent bodily tissue.

While the catheter or probe is constructed of a biocompatible material, protective mechanisms of the body generally operate on the invasive device to protect the body from the invasion of the foreign object. The most common protective mechanism of the body is encapsulation of the foreign object by a growth of isolating tissue. Obviously, the encapsulation of the end of the catheter or probe from which the sensor or electrode protrudes will significantly reduce or cease desired function of the in vivo device. Further, and in particular with regard to a catheter placed within a blood vessel, blood clotting may occur at the end of the catheter where a sensor extends or is exposed resulting in reduced effectiveness of the in vivo device, as well as blockage of the vessel by the clot. This is clearly an undesirable result.

Antithrombogenic chemical substances are known which reduce and slow the formation of thrombus, tissue growth, blood clotting and the encapsulation mechanism. For example, the substance known as "heparin" is a known anticoagulant which inhibits the action of the enzyme thrombin in the final stage of block coagulation. Heparin is generally applied in dilution in saline solution. The use of such substances with catheters and probes to reduce the undesirable effects of the body's protective mechanisms has been taught. For example, U.S. Pat. No. 4,954,129, issued to Giuliani, et al., teaches the use of theses chemical substances for hydraulic flushing of thrombus or clotting material from within the lumen of an intravascular catheter having an open end from which a sensor probe extends. The Giuliani et al. disclosure further provides a defined process for flushing the bore of the catheter which utilizes a periodically increased velocity pulse of a flushant to remove incipient clot material formations. A specific structure is described and claimed for centering a sensor probe within the lumen of the catheter and away from the catheter wall which provides fluid channels for the flow of the flushant through and from the end of the catheter around the probe sensor.

Another U.S. Pat. No. 4,934,369, issued to Maxwell, deals with the subject problems in a similar manner. While Maxwell teaches the technique of flowing antithrombogenic fluid through and out of the end of the intravascular catheter around the sensors for measuring blood constituents, he also teaches the positioning of the sensors within the catheter lumen a select distance from the opening at the end of the catheter. Blood is permitted to enter the end of the catheter and/or through ports about the circumference of the catheter and mix with the antithrombogenic fluid to forming an interface zone therebetween. The blood-fluid interface zone is washed back and forth over the sensors to expose the sensors to both blood and antithrombogenic fluid by one of various described means for pulsing the flow of fluid within the catheter lumen.

While these references appear to disclose functional systems for applying an antithrombogenic fluid to the environment of a sensor, both concern catheters which have an opening at their distal end which permit the sensor exposure to blood, either by the sensor extending through the opening to come into contact with blood, or by blood entering the end opening to contact the sensor immediately adjacent therewith. In both constructions the antithrombogenic fluid flows through the lumen of the catheter and exits the end of the catheter, requiring some means to position the sensor centrally within the end opening in order for it to obtain uniform exposure and for uniform fluid infusion. Such configurations require constructions of complex design which, of course, substantially increase cost. The Maxwell design, for example, is subject to sensitive dynamic control to assure proper and effective association of the sensor with blood entering the end opening of the catheter. The Giuliani et al. design consists of tortuous surface shapes in the bore and adjacent to the end of the catheter, all of which provide fertile areas for the incipiency of thrombus or clot formation, in direct opposition to the intended purpose. Tooling used during manufacture is complex and expensive. Further, with the Giuliani et al. design, sensor positioning within the catheter and in relation to the end opening becomes a critical parameter for effective operation, which proper positioning is difficult to ascertain once the catheter has been inserted into a patient's blood vessel.

It is thus apparent that improvements are needed in the way in which select fluids or liquid chemicals are introduced to an in vivo sensing or stimulating location for the purpose of reducing the undesirable effects of the body's protective mechanisms.

SUMMARY OF THE INVENTION

The present invention addresses the above and other needs by providing a fluidic infusion system for introducing a select liquid chemical into the environment surrounding the functional end of an in vivo catheter or probe. Such system comprises a catheter or probe having a sensor or electrode positioned near or at its closed distal end. A plurality of spaced radial openings are formed adjacent to the end of the catheter or probe for introducing the select liquid chemical into the appropriate environment. The catheter or probe has at least one lumen extending through its length for directing the liquid chemical from a controlled pump to the radial openings. The radial openings are positioned within the catheter or probe so that when the catheter or probe is inserted into the appropriate environment, e.g., within a blood stream inside or an artery or vein, the radial openings are upstream from the sensor or electrode relative to the flow of blood within such environment. In this manner, the natural flow of blood carries the liquid chemical from the radial openings to the sensor or probe area, where it can perform its intended function.

In accordance with one aspect of the invention, the catheter or probe may include a plurality of lumens for transporting differing liquid chemicals to the concerned environment.

In accordance with another aspect of the invention, the pump that causes the liquid chemical to flow through the lumen is controlled to meter the flow of fluid from the catheter or probe, and preferably is also controlled to cease the flow of fluid during periods when the sensor or electrode borne by the catheter or probe is performing its objective function. Multiple pumps may be used with a multi-lumen catheter or probe, each transporting and metering a different fluid through an individual lumen.

In accordance with yet an additional aspect of the invention, the fluidic lumen(s) through the catheter or probe are protected from closure caused by the clotting of fluids received from the surrounding environment. Such protection is afforded by use of antireversion means that prevents reversion flow through each of the radially extending ports from the environment into the fluidic lumen(s). In other words, such protection restricts the flow of fluid through the openings or ports to one direction. Fluid is permitted to flow from the lumen to the outside environment where the probe or catheter is placed, but is not permitted to flow from the outside environment into the lumen. Such antireversion means comprises, e.g., a resilient closure means or flap which only permits fluid flow from within the catheter through each port to the concerned environment, and prevents reversion flow of fluid through the port.

The fluid infusion system of the present invention may be used to introduce a liquid chemical which effectively prevents, or reduces, formation of thrombus, tissue growth and encapsulation of the invasive portion of the catheter, which medicates and prevents infection at the site of implantation, which anesthetizes surrounding neurostructure, or which applies a calibration or control substance into the investigated environment.

In a preferred embodiment, wherein a plurality of fluidic lumens are formed through the catheter or probe, each lumen connecting with an individual controlled pump and opening to the environment through one or more of the radial ports, it is one feature of the invention that a select combination of liquid chemicals may be advantageously introduced into the surrounding environment with precisely metered precision and without concern of mixing the differing liquid chemicals prior to such introduction.

It is another feature of the invention to utilize the body's own natural flow of fluids, e.g., the natural flow of blood within an artery or vein or body organ, to carry the introduced fluid chemical to the region of concern whereat the sensor or electrode is positioned.

BRIEF DESCRIPTION OF THE DRAWINGS

The above and other aspects, features and advantages of the present invention will be more apparent from the following more particular description thereof, presented in conjunction with the following drawings, wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
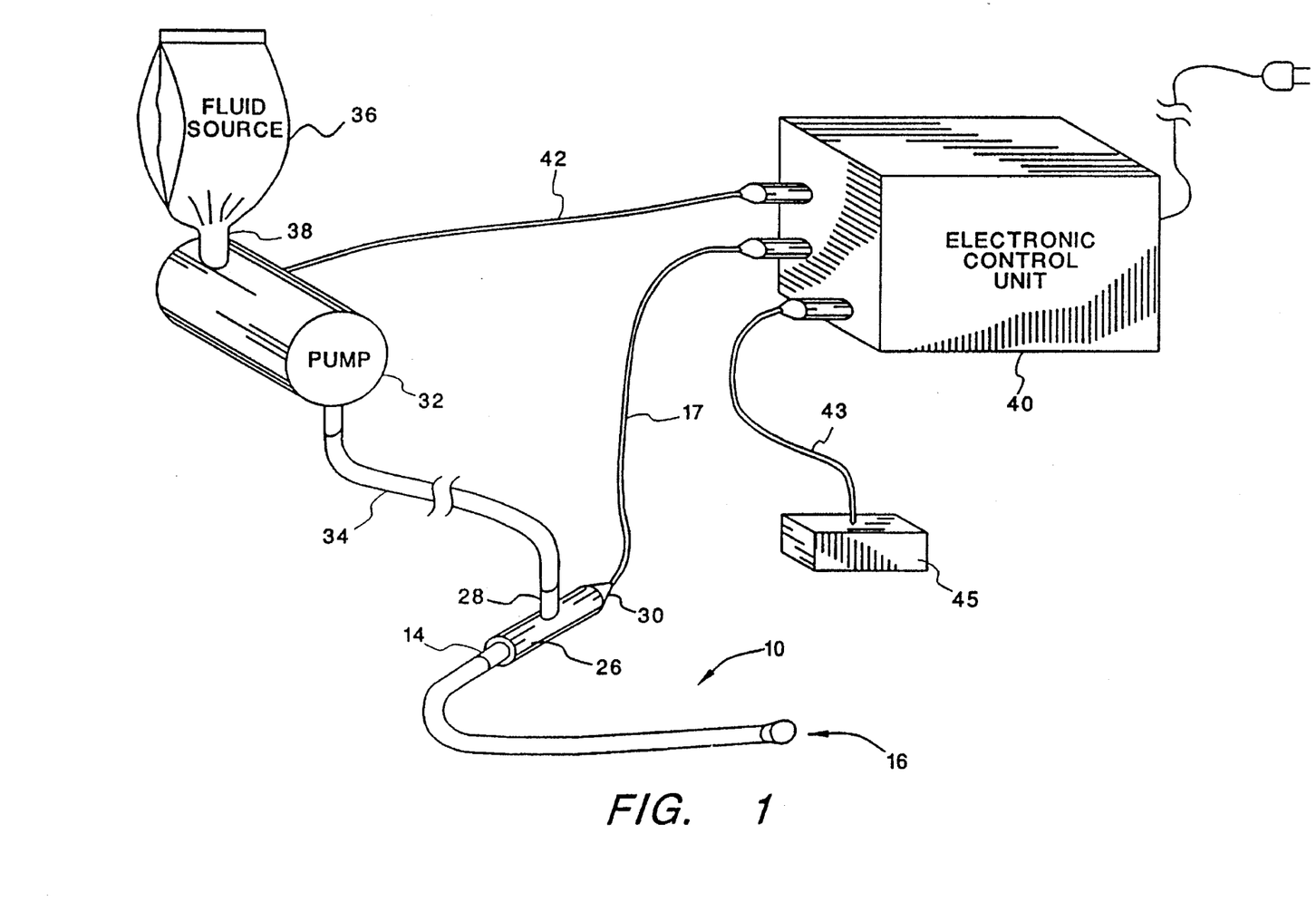
FIG. 1 is a schematic drawing of a fluidic infusion system made in accordance with the invention for introducing a select liquid chemical into the environment surrounding the functional end of an in vivo catheter or probe.
Figure 2A:
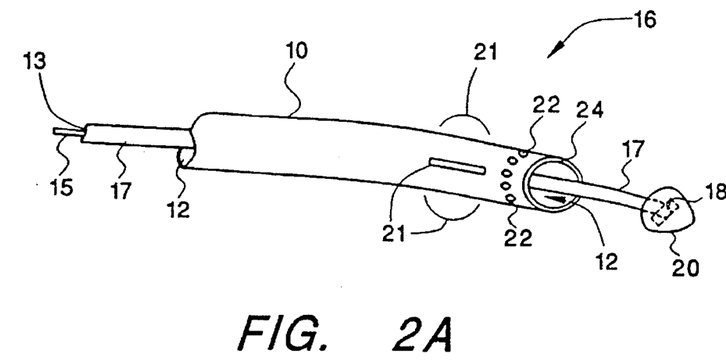
FIG. 2A is an enlarged view of the implanted end of the in vivo catheter or probe in accordance with one embodiment, wherein the material that closes the end of the catheter or probe embodies the sensor or electrode, and wherein such material is shown in an exploded manner separated from the end, and with a partial section removed from the side of the catheter or probe to show the fluidic lumen extending through the length thereof.
Figure 2B:
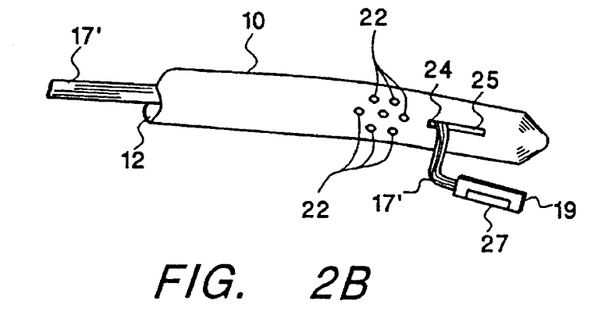
FIG. 2B is an enlarged view of the implanted end of the in vivo catheter or probe in accordance with another embodiment, wherein the sensor or probe is positioned at a side window near the closed end of the catheter or probe, and wherein such sensor or probe is shown in an exploded manner separated from the side window, and further wherein a partial section of the catheter or probe is removed to show the fluidic lumen extending through the length thereof.

A fluidic infusion system for introducing a select liquid chemical into the environment surrounding the functional end of a catheter or probe 10 is shown in FIGS. 1, 2A and 2B. The catheter/probe 10 is placed within the body relative to the vascular or neurological anatomy of a patient, and performs a measurement, sensing or stimulation function. The catheter 10 has a lumen which extends through its length from a commencing or proximal end 14 to a distal end 16. The lumen forms an opening at the commencing end 14 of the catheter which receives the select liquid for transport to the opposing distal end 16 which is closed at the end. Expanded views of representative configurations of the distal end 16 that may be used with the invention are shown in FIGS. 2A and 2B.

In FIG. 2A, for example, a conductor 17 is connected to a sensor or electrode 18 at the distal end 16. The conductor 17, which typically comprises a conductive member 15 encapsulated within an insulating sheath 13, enters the opening in the commencing end 14 of the catheter and extends through the lumen 12 to the distal end 16 of the catheter where the sensor 18 is positioned. The sensor 18 is mounted at the distal end 16 in a porous or semi-porous material 20 which closes the lumen 12 at the distal end 16. The porosity of the material 20 permits investigated bodily fluids to reach the sensor 18 so that it will effectively perform the desired measurement or sensing function. A plurality of openings 22 are formed through a wall 24 of the catheter 10 which permit liquid transported through the lumen 12 to pass into the environment surrounding the distal end 16 of the catheter. For the embodiment shown in FIG. 2A, the openings 22 are circumferentially spaced around the catheter 10 and are axially spaced from the material 20 in which the sensor 18 is held by a select spacing, which may be as close as 0.001 inches, or as far as 30 or more inches, depending upon the application of the catheter and the body tissue or fluid into which it is implanted. For most human applications, the openings will be no more than about 1.0 inch from the sensor 18. The number of openings 22 which are formed may be selected as deemed appropriate, but at least 3 openings are preferably used to obtain effective introduction of the liquid around the entirety of the distal end 16 of the catheter. The diameter of the openings is as large as is necessary to obtain adequate liquid flow into the environment surrounding the distal end 16 of the catheter for the particular application with which the catheter 10 is used. Further, centering nubs 21 may be placed near the openings 22 in order to assure that an adequate flow of fluid may exit through the openings 22 by keeping the catheter spaced apart from an arterial or venus wall that might otherwise block the openings 22.

In FIG. 2B, a side-looking or window sensor 19 is positioned so that an active area 27 thereof is exposed through a window 25 in the wall 24 of the catheter 10. A plurality of openings 22 are arranged in a suitable pattern near the window 25, somewhat closer to the proximal end 14 of the catheter than is the window 25. The spacing between the openings 22 and the window 25 is typically between about 0.001 and 30.0 inches, depending on the application. For most human applications, the sensor window may be, e.g., no more than about 1.0 inches from the opening 22. A ribbon cable 17', comprising a plurality of separate electrical conductors, or equivalent multi-conductor cable, makes electrical connection with the sensor 19, as required. Sensors suitable for use with the present invention may measure glucose concentration, oxygen, pH, temperature, or other physiological parameters of interest. Representative sensors are described, e.g., in U.S. Pat. Nos. 4,627,906; 4,671,288; 4,703,756; 4,781,798; 4,815,469; or in U.S. patent application Ser. No. 08/155,737, filed Nov. 19, 1993; all of which are incorporated herein by reference.

Figure 3:
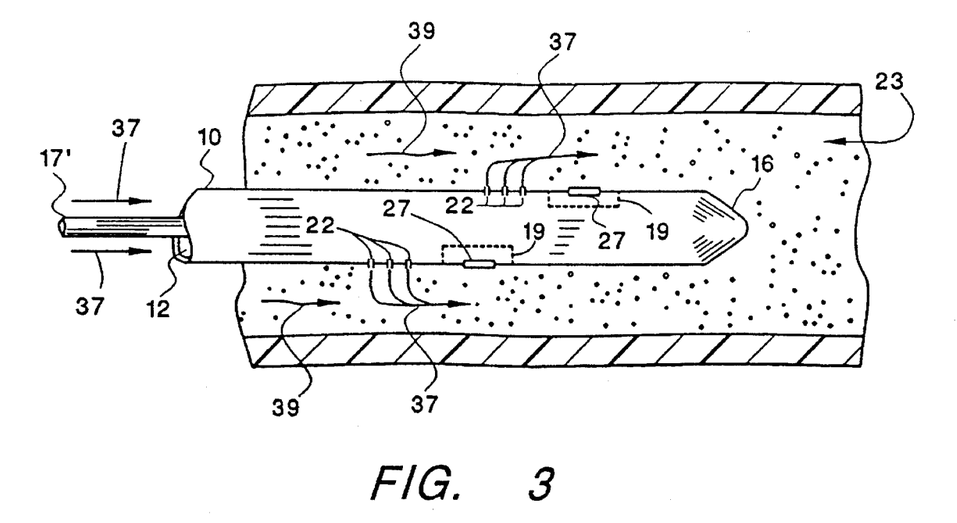
FIG. 3 depicts the in vivo placement of the catheter or probe within a blood vessel, and illustrates the use of a plurality of side sensors or probes along the length of the catheter or probe near its closed end, and further shows the introduction of a liquid chemical into the blood vessel through ports upstream from the side sensors or probes, thereby allowing the flow of blood to carry the introduced liquid chemical past the respective side sensors or probes.

In FIG. 3, the in vivo placement of the catheter 10 within a blood vessel 23 is shown. The blood vessel 23, which may be either an artery or a vein, has a blood 39 flowing therein. The direction of blood flow is represented by the arrows 39. FIG. 3 illustrates the use of a plurality of side-looking sensors/probes 19, each having an active area 27 exposed through a corresponding window 25 within the side wall 24 of the catheter 10. The active area 27 of each sensor/probe 19 is positioned along the length of the catheter 10 near its distal end 16. As explained above, the catheter 10 has a lumen 12 therein through which a cable 17' makes electrical contact with the sensors 19. In operation, a suitable chemical liquid 37 (represented by the arrows 37) is introduced under pressure (i.e., pumped) into the lumen 12. Such chemical liquid 37 exits the lumen 12 into the blood stream 39 through the openings 22 that are positioned just upstream from the windows 27 of the sensors/probes 19. Hence, the flow of blood carries the introduced chemical liquid 37 past the respective active area 27 of each side-looking sensor/probe 19.

Figure 4A:
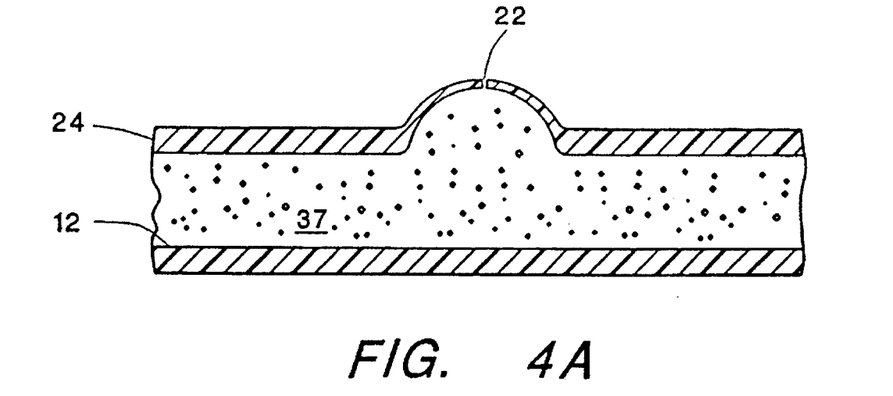
FIGS. 4A through 4D are fragmentary sectional views of various designs of the antireversion means used by the invention to prevent reversion flow through the ports or openings of the catheter or probe through which the liquid chemical is introduced.
Figure 4B:
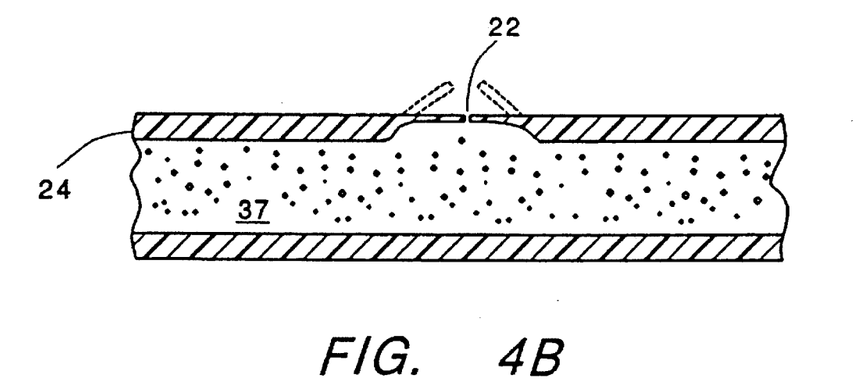

Preferably, each of the openings 22 includes an antireversion means for preventing reversion flow of bodily fluids from the environment surrounding the distal end 16 of the catheter 10 into the lumen 12. The antireversion means protects the lumen 12 from closure by thrombosis of any fluid which may enter into the lumen from the surrounding environment. The means for preventing reversion flow may be a resilient material, such as silicone rubber, in or around the opening 22 in which a pore or slit is formed as shown in FIGS. 4A and 4B. Such pore or slit remains closed unless the pressure of the chemical liquid 37 is sufficient to force the liquid 37 through the pore or slit. Advantageously, the pressure of the liquid within the catheter may be readily controlled through selective activation of the pump 32 (FIG. 1).

Figure 4C:
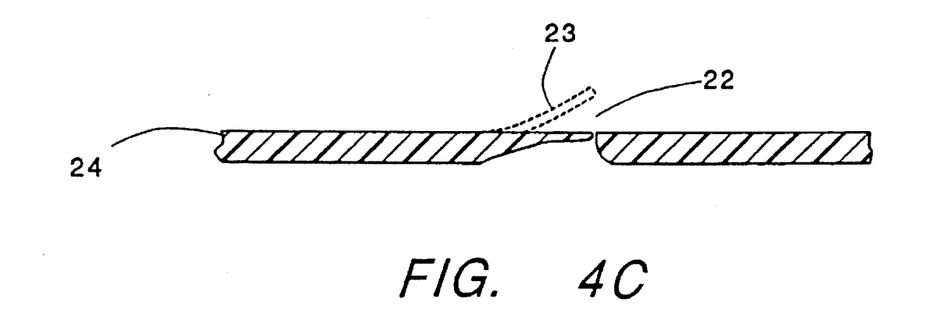
Figure 4D:
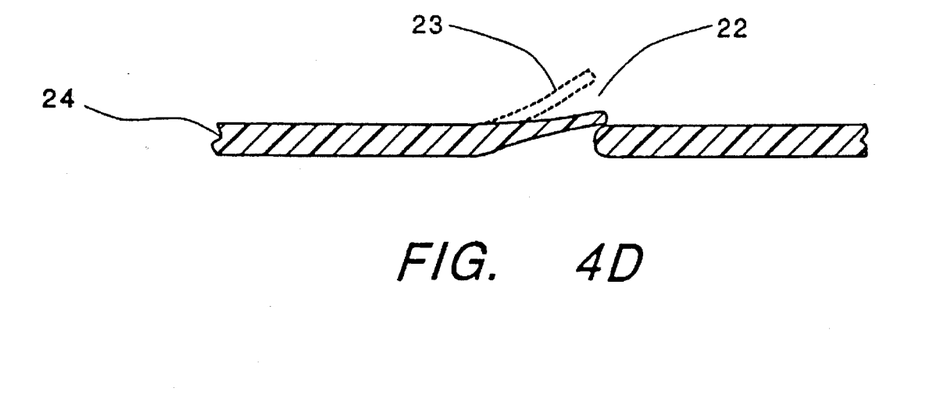

Alternatively, a flap 23, of flexible material may be formed in or over the opening 22 as shown in FIGS. 4C and 4D. The flap 23 remains closed, and thereby prevents reversion of bodily fluids into the catheter 10, as long as the pressure of the liquid within the lumen of the catheter is less than the pressure on the outside of the catheter. Conversely, the flap 23 opens, and thereby allows the liquid within the lumen of the catheter to exit through the opening 22 to the outside of the catheter whenever the pressure of the liquid within the lumen is greater than the pressure on the outside of the catheter. As with the antireversion means shown in FIGS. 4A and 4B, the pressure of the liquid within the catheter may be readily controlled, as desired, through selective activation of the pump 32 (FIG. 1).

Thus, it is seen that through the use of antireversion means such as is shown in FIGS. 4A, 4B, 4C or 4D, or equivalents thereof, fluid flow is permitted only from within the catheter lumen 12 through each opening 22 to the concerned environment, and fluid flow is prevented from the environment outside the catheter lumen 12 through each opening 22 into the lumen 12.

Figure 4E:
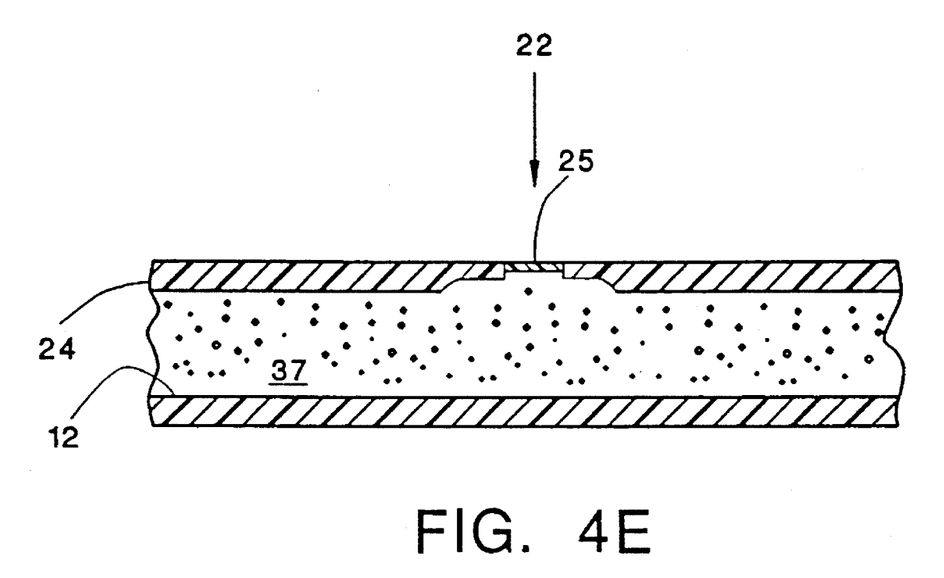
FIG. 4E shows a sectional view of a catheter wherein a prescribed membrane plugs the radial hole in the catheter wall, and wherein the membrane allows molecules of a prescribed size or smaller to pass therethrough.

An alternative to the antireversion means shown in FIGS. 4A–4D is to use a membrane 25, such as is shown in FIG. 4E, in place of the opening 22. The membrane 25 is made from a material, such as Hema or polyurethane, that allows the passage of small molecules therethrough. However, larger molecules are prevented from passing through the membrane 25. Thus, small molecules, such as those of glucose, readily pass through the membrane 25; but large molecules, such as blood, do not. Use of the membrane 25 advantageously allows the outer surface of the catheter 10 to remain smooth, without any sharp points or edges, which sharp points or edges could otherwise contribute to the formation of blood clots.

Referring momentarily again to FIG. 1, it is seen that the commencing end 14 of the catheter 10 is mounted to and is in fluid communication with a manifold 26 which permits both the select liquid chemical 37 and the electrical conductor 17 or 17' to be received in the opening formed by the lumen 12 at the commencing end 14. The manifold 26 has a fluid entry port 28 for receiving the liquid chemical 37. Further, the manifold 26 has a sealed entry site 30 for the electrical conductor 17 or 17'. More than one fluidic entry port may be provided. In particular, multiple entry ports specifically communicating with one of a plurality of lumens may be provided as discussed further below in connection with FIG. 6.

The fluid entry port 28 of the manifold 26 is connected to a pump 32 through a fluid conduit 34. The select liquid chemical 37 is stored in a reservoir 36 and transported to the pump 32 through a supply conduit 38. Operation of the pump 32, and the measurement, stimulating or sensing function performed by the sensor/probe 18 or 19 is controlled and performed by an electronic control unit 40, which is described below in conjunction with FIG. 5. The control unit 40 electronically communicates with the pump 32 and the sensor/probe 18 or 19 through electrical conductors 42 and 17 (or 17') respectively.

An additional sensor 45 may be coupled to the control unit 40 by way of an additional electrical cable 43. Such sensor 43, when used, provides supplementary information relative to the patient or the patient's environment wherein the catheter 10 is implanted. For example, such additional sensor 45 may sense body temperature, respiration rate, perspiration, movement, or any other parameter that provides supplementary patient information that may be useful in the control of the pump 32 and the infusion of the liquid chemical to the site of the implanted probe or sensor 18 or 19.

Figure 5:
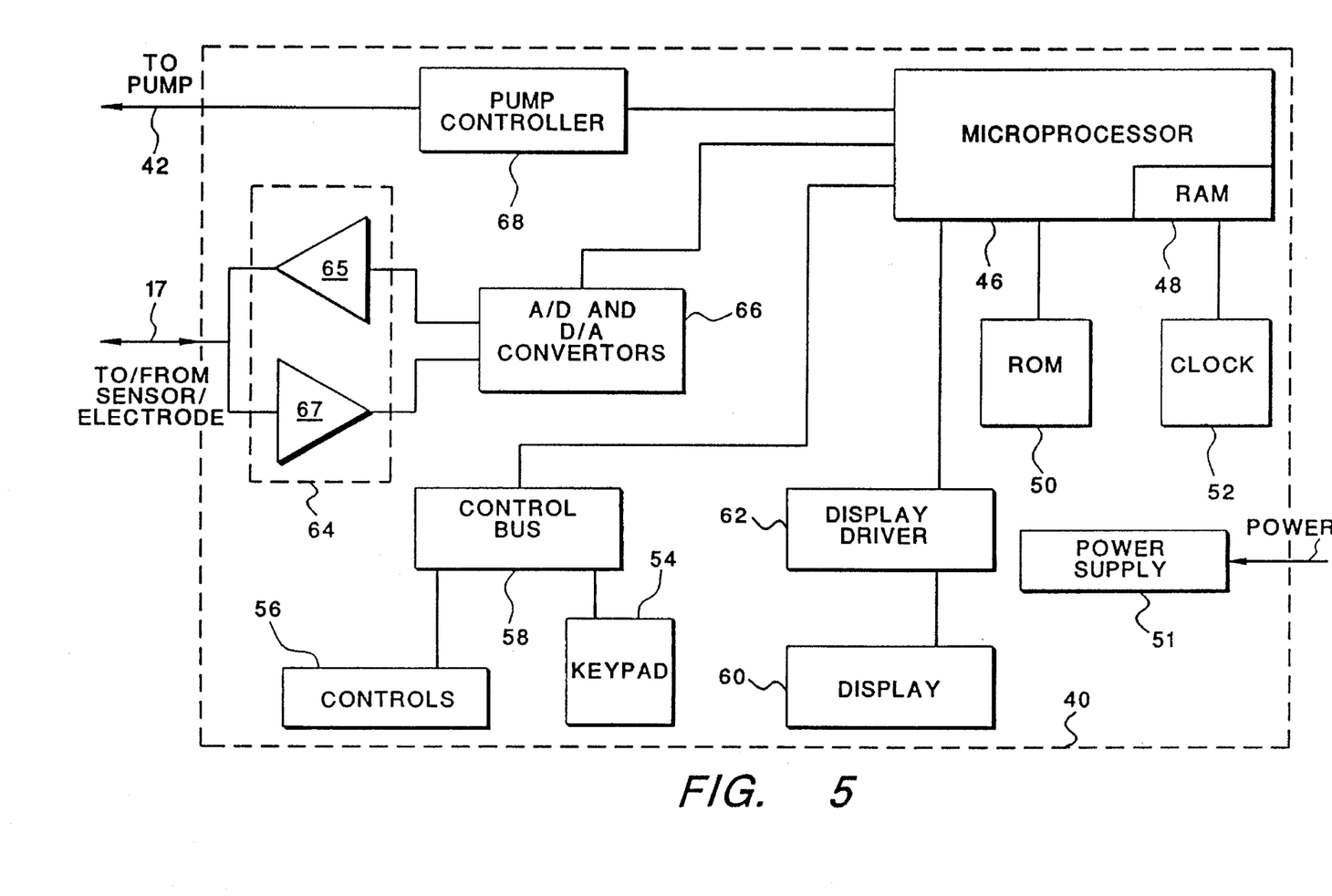
FIG. 5 is a functional block diagram of the electronic control unit of FIG. 1, which electronic control unit is used to meter the flow of the liquid chemical through the lumen of the catheter or probe, and is also used to control and/or monitor the operation of the sensor(s) or electrode(s) located within the catheter or probe.

Referring next to FIG. 5, a functional block diagram of one embodiment of the electronic control unit 40 is shown. While the described embodiment clearly teaches the operational characteristics required of the control unit 40 to operate the fluidic infusion system so as to provide the desired flow of fluid to the catheter or probe, and while such embodiment shows the basic elements concerning operation of the sensor or electrode to provide the desired measurement, sensing or stimulation function, it is noted that alternative and differing electronic constructions for providing the described functions may be utilized.

As seen in FIG. 5, the fluid infusion system for introducing liquid chemical into the environment surrounding the functional end of an in vivo catheter or probe is driven by a microprocessor 46, which is the foundation of the control unit 40. The microprocessor 46 is supported by programmable and non-volatile memory, depicted as a RAM electronics block 48 and a ROM electronics block 50, and by a clock circuit 52. The clock circuit provides a clock signal that serves as a timing reference for all system activity. A suitable microprocessor, including the above described elemental component electronics, may be selected as one of a number of commercially available computer chips from companies such as Intel or Texas Instruments which are useable to perform the herein described functions of the control unit 40. Alternatively, the microprocessor may be custom designed through well known design methods and criteria as the specific application warrants.

Programmable memory of the microprocessor 46 and variable system functions driven by the microprocessor 46 are programmed or set through a keypad 54 or other system controls 56, i.e., rotary switches or the like. Such controls 56 and/or keypad 54 interface with the microprocessor 46 through a suitable control bus 58 in order to communicate desired function and input information to the microprocessor, thereby directing such microprocessor to perform a desired function.

Differing system functions which may be selectable through the controls 56 and/or keypad 54 may include, for example: (1) infusing a prescribed quantity of the desired liquid chemical to the sensing/stimulating site over a fixed period of time (and thereby fixing the rate at which the desired liquid chemical is infused) for the purpose of, e.g., fighting an infection, treating pain, removing clots, or the like; (2) measuring a selected parameter through the sensor or probe 18 or 19 and displaying the results thereof; (3) testing the efficacy of the sensing/stimulating function in the presence of varying amounts of the chemical liquid; (4) calibration; (5) setting operational limits and alarms; (6) repairing and/or unclogging a stopped-up catheter; (7) dissolving blood clots that are hampering the function of an implanted sensor; (8) providing optical clarity for fiber optic viewing, or for optimum operation of sensing/stimulating systems (e.g., prior to releasing chemotherapy drugs); or (9) temporarily increasing or decreasing the electrical impedance in the vicinity of a catheter tip (e.g., by injecting a small amount of a prescribed chemical or liquid); and the like.

Information of the measurement, sensing or stimulation function being performed and of system set-up and operation is communicated to an operator through a visual display 60, such as a cathode ray tube (CRT) or liquid crystal display (LCD). The display 60 is driven in response to output signals from the microprocessor 46 through an appropriate display driver 62, using techniques and procedures well known in the art.

Input and output informational signals supplied to or received from the sensor or electrode 18 or 19 are communicated through a suitable signal conditioning circuit 64. Such circuit includes, e.g., in the case of signals being transmitted to the sensor/electrode, a suitable line driver circuit 65. In the case of signals being received from the sensor/electrode 18 or 19, such circuit includes a suitable low noise amplifier 67. Appropriate analog-to-digital (A/D) and digital-to-analog (D/A) conversion is performed using A/D and D/A converters 66. The A/D portion of convertor circuit 66 converts the analog signal produced by the sensor (18 or 19) to a digital signal receivable by the microprocessor 46. Conversely, a D/A portion of the convertor circuit 66 converts digital signals issued by the microprocessor 46 to an analog control signal for driving an implanted stimulating electrode, or controlling an implanted sensor. In the case of a stimulating pulse that is delivered to a stimulating electrode, conventional analog circuits may be used to generate the stimulation pulse, with a trigger signal generated by the microprocessor being used to control when the stimulation pulse is delivered to the stimulating electrode.

Control signals for controlling operation of the pump 32 are provided by the microprocessor 46 to a suitable pump controller circuit 68. In response to such control signals, the pump controller 68 drives the pump operation to control fluid flow and fluid flow rate to the environment surrounding the implanted end 16 of the catheter or probe 12.

Program control information is stored within the memory 48 and/or 50 of the control unit 40. Such control information is used by the microprocessor 46 to, e.g., select a range of variable fluid flow rates for introduction of fluid into the concerned environment, or to control or set other parameters used by the control unit 40. Such programming instructs the microprocessor 46 to generate correct control signals for application to the pump controller 68 in order to drive the pump 32 at the desired flow rate. Additionally, the microprocessor memory 48 and/or 50 is preferably programmed to provide a synchronization control function whereby the pump 32 is controlled to stop fluid flow from the catheter or probe for a selectable time period during performance of the measurement, sensing or stimulation function by the embodied sensor or electrode. That is, the fluid is pumped to flow to the stimulation or sensing site, and then the fluid is stopped for a time, while the stimulation or sensing function is carried out. This sequence of pumping, stopping, and sensing/stimulating repeats as controlled by the control information stored in the memory 48 and/or 50.

The control unit 40 is designed and assembled with commonly available components using techniques, methods and criteria well known to engineers and technicians working in the electronic arts to provide the functional characteristics sought and described above.

Figure 6:
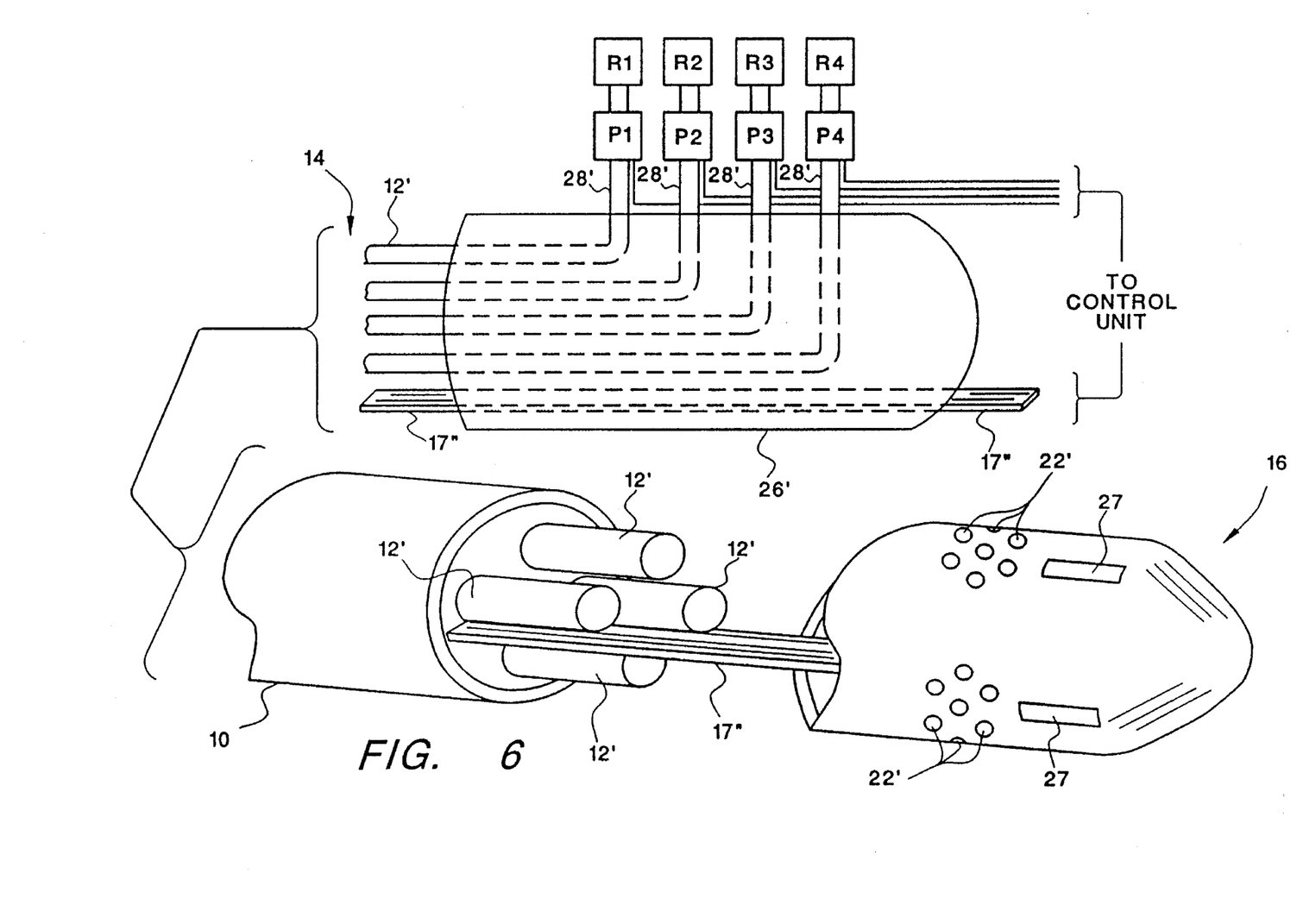
FIG. 6 shows an enlarged view of one embodiment of the implanted end of the in vivo catheter or probe of the present invention with a partial section removed from the side of the catheter or probe to show multiple fluidic lumens extending through the length thereof, and schematically depicts how a plurality of pumps are used to control the flow of a respective liquid chemical through each lumen.

In another form, shown in FIG. 6, the catheter or probe 10 may have a plurality of lumens 12' extending through its length from the commencing end 14 to the closed distal end 16. Each of the lumens 12' transports a different fluid to one or more of the openings 22' formed in the distal end 16 of the catheter. Typically, the fluid is each lumen remains separated from the other fluids in the other lumens until just before the location of the openings 22'. At that point, the fluids mix in an enclosed chamber (i.e., where all the lumens 12' join to form one large lumen), and the resulting mixed fluid then exits through the openings 22', just upstream from the active portion 27 of the sensor or electrode. Alternatively, separate openings 22' may be connected to respective lumens 12' so that mixing of the chemical liquids does not occur until the chemical liquids have exited the catheter 10.

At the commencing end 14, each of the lumens 12' or select groups of them, have individual pumps P1, P2, P3, P4 coupled to respective liquid reservoirs R1, R2, R3, R4, in order to supply a desired liquid chemical to the appropriate lumen. (The use of four lumens, four pumps, and four reservoirs is only exemplary, as any plurality of lumens, pumps and reservoirs could be used.) A manifold 26' having cooperating multiple entry ports 28' mating with the lumens 12' for transport of fluids to the site of implantation facilitates such multiple liquid chemical delivery. Such configuration advantageously permits differing liquid chemicals to be transported to the site of implantation without being mixed until they are introduced into the surrounding environment, while obtaining accurate metering of the volume of each liquid chemical.

Each of the individual pumps P1, P2, P3, P4 is controlled by the control unit 40 and the microprocessor 46 to individually provide desired fluid flow for the select liquid chemical which it transports in the same manner as described above for a singular pump 32. All or select ones of the individual pumps P1, P2, P3, P4 may be operated by the control unit 40 under the above described synchronization control function whereby all or select ones of the pumps P1, P2, P3 or P4 are controlled to stop flow of a select liquid chemical from the catheter or probe for a selectable time period during performance of the measurement, sensing or stimulation function by the embodied sensor or electrode.

In a further alternative embodiment, the pump, reservoir and catheter systems may be implanted within the body and controlled by an external controller via a telemetric communications system, such as described in U.S. Pat. No. 4,871,351 issued to Feingold; or U.S. Pat. No. 4,944,299, issued to Silvian, both of which patents are incorporated herein by reference.

Turning next to FIG. 8, a simplified flow chart is shown that depicts, in accordance with one embodiment of the invention, two control loops that are carried out by the microprocessor 46 of the control unit 40 as it controls the infusion of the desired liquid through a single lumen to the sensing or stimulating site. Each main step or operation carried out by such control is depicted in the flow chart as a "box" or "block", each having a reference numeral. While such flow chart illustrates the operation of the invention for the single lumen embodiment depicted in FIGS. 1–3, it is to be understood that a similar flow chart may be used, expanded as needed, for the multiple lumen embodiment of the invention shown in FIG. 7. In the description that follows, the reference numerals used refer to both the block of the flow chart being described, or to the block diagram of FIG. 1, or the views of the distal end of the catheter shown in FIGS. 2A, 2B or 3.

Figure 7:
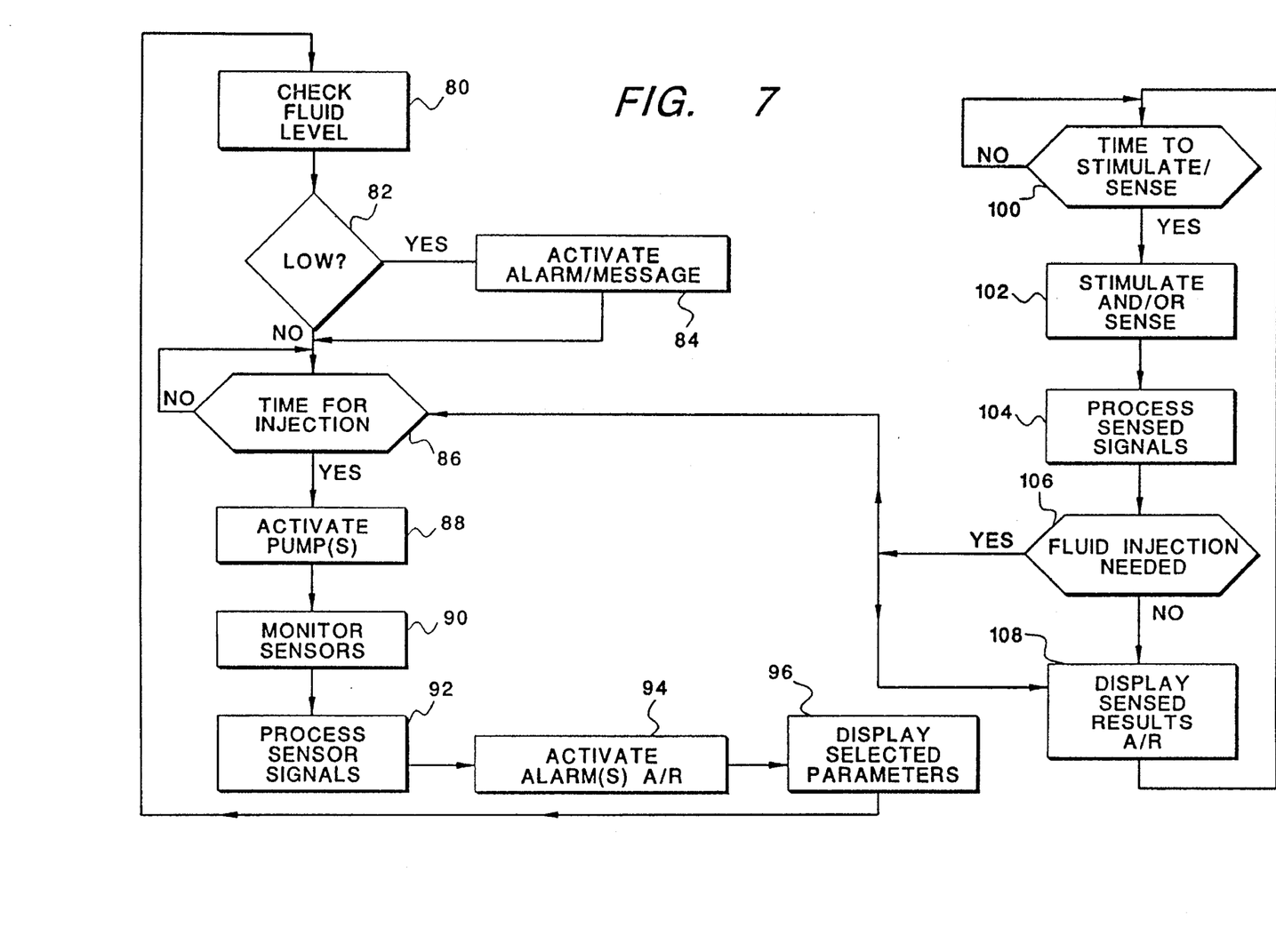
FIG. 7 is a flow chart illustrating one method used by the electronic control unit of FIG. 5 to use feedback information obtained from the sensor/probe to control, at least partially, the amount or rate of liquid chemical that is metered to the site of the sensor or probe through the fluidic infusion system.

A first loop of the control method shown in FIG. 8 begins by checking the fluid level (block 80) in the fluid source reservoir 36. If it is low (block 82), then an appropriate alarm or alarm message is activated (block 84). Such alarm or alarm message may utilize a separate audible alarm (e.g., a speaker that emits a beep) that forms part of the controls 56 of the control unit 40, and/or an alarm message that is flashed or otherwise displayed prominently on the display 60.

Next, a determination is made as to whether it is time for an injection of the fluid to be made to the implant site (block 86). Such determination may be made, e.g., through use of a programmable timer that injects a prescribed amount of the liquid chemical on a regular basis, e.g., once every one or two minutes. Conjunctively, or alternatively, such determination may be made based on a feedback signal obtained from the sensor(s) used as part of the invention, explained below.

If it is time for an infusion of the liquid chemical, then the pump is activated (block 88) for the prescribed time. After the pump has delivered the liquid chemical to the implant site for the prescribed period of time, then the pump is preferably deactivated and the sensor(s) are monitored (block 90). Such sensor(s) may include the sensors 18 or 19 that are located at or near the distal tip 16 of the implanted catheter 10, and/or other sensors 45 that may be coupled to the control unit 40. The signals obtained from the sensor(s) are then processed (block 92). Depending upon the options that are selected, if the processed sensor signals indicate that prescribed limits have been exceeded, then an appropriate alarm is activated (block 94). For example, it the sensor monitors body temperature, and if the body temperature exceeds a preset limit, then an alarm message may be generated. Further, selected parameters obtained from or related to the processed sensor signals are displayed (block 96). Then, the process repeats by again cycling through the first loop, i.e., by carrying out the functions indicated in blocks 80–96.

Concurrent with the control of the pumps and infusion of the liquid chemical carried out by the first control loop described above, is a second control loop. The second control loop operates in parallel with the first control loop, but is preferably synchronized with the first control loop so that appropriate actions (such as monitoring the sensors and stimulating) do not occur simultaneously. In the second control loop, a determination is made as to whether it is time to stimulate or sense (block 100) using the appropriate sensor or electrode at or near the distal tip 16 of the catheter 10. If so, then an appropriate control signal is generated that causes the stimulation or sensing function to be performed (block 102), e.g., a stimulation pulse is generated, or a sample of the sensing signal is taken.

Next, any sensed signals obtained as a result of such stimulation or sensing are processed (block 104). Based on such processing, a determination is made as to whether a fluid injection of the liquid chemical is needed (block 106). Such determination is dependent upon the particular application of the invention that is being used. For example, if after stimulation it appears that the stimulation did not evoke the desired response, then a determination may be made that an infusion of the liquid chemical is needed to remove a possible tissue growth or encapsulation at the electrode. Or, for example, if after sensing blood oxygen, a reading is obtained that is out of range, a determination may be made that an infusion of the liquid chemical is needed to perform a calibration or to remove a possible thrombus or blot clot that may have formed on the sensor window. In this manner then, a determination is made as to the effectiveness or accuracy of a particular stimulation or sensing function, and the liquid chemical is then controllably infused, as needed, to improve the stimulation or sensing function. If a determination is made that a fluid infusion is needed (YES branch of block 106), then such determination is made to the first control loop, described above. Further, regardless of whether a fluid injection is needed, any sensed results associated with the stimulation or sensing (carried out at block 100) may be displayed (block 108).

As described above, it is thus seen that the invention provides a fluid infusion system that introduces a liquid chemical at a sensing or stimulating location that effectively prevents, or reduces, formation of thrombus, tissue growth and encapsulation of the invasive portion of the catheter, that medicates and prevents infection at the site of implantation, that anesthetizes surrounding neurostructure, or that applies a calibration or control substance into the investigated environment.

As further described above, it is seen that a plurality of fluidic lumens may be used within the catheter or probe, with each lumen connecting with an individual controlled pump and opening to the environment through one or more of the openings or ports, thereby enabling a select combination of liquid chemicals to be introduced into the surrounding environment with precisely metered precision and without concern of mixing the differing liquid chemicals prior to such introduction.

As also seen from the above description, the invention advantageously utilizes the body's own natural flow of fluids, e.g., the natural flow of blood within an artery or vein or body organ, to carry the introduced fluid chemical to the region of concern whereat the sensor or electrode is positioned.

While the invention herein disclosed has been described by means of specific embodiments and applications thereof, numerous modifications and variations could be made thereto by those skilled in the art without departing from the scope of the invention set forth in the claims.

What is claimed is:

1. An infusion catheter or probe for in vivo placement having a tubulus configuration, said catheter or probe comprising:

at least one axially extending lumen through which fluid is transported from an opening formed by said lumen in a commencing end of said catheter or probe to a closed distal end thereof;

a plurality of circumferentially spaced radial openings formed through said catheter or probe communicating with said fluidic lumen to introduce fluid into the environment surrounding the distal end of the catheter or probe, said radial openings being axially spaced from said distal end by a select spacing; and a sensor/electrode proximate the distal end of said catheter or probe to perform a measurement, sensing or stimulation function together with said introduction of fluid into the environment surrounding the distal end of the catheter or probe.

2. The infusion catheter or probe of claim 1 wherein said radial openings formed in said catheter or probe are each axially spaced the same distance from the sensor/electrode.

3. The infusion catheter or probe of claim 1 wherein said radial openings formed in said catheter or probe are axially spaced at varying distances from the sensor/electrode.

4. The infusion catheter or probe of claim 1 wherein each of said radial openings is plugged with a membrane that permits molecules less than a prescribed size to pass therethrough, and blocks molecules having a size greater than the prescribed size from passing therethrough.

5. The infusion catheter or probe of claim 1 wherein said radial openings formed in said catheter or probe are axially spaced from the sensor/electrode by a distance that is less than about 1.0 inch.

6. The infusion catheter or probe of claim 1 wherein said catheter or probe has a plurality of axially extending lumens through which fluid(s) is transported from openings formed by said lumens in the commencing end of said catheter or probe to the closed distal end thereof, each of said lumens communicating with at least one of said plurality of circumferentially spaced radial openings formed through said catheter or probe to introduce said fluid(s) into the environment surrounding the distal end of the catheter or probe.

7. The infusion catheter or probe of claim 1 wherein each radial opening formed through said catheter or probe additionally comprises means for preventing reversion flow of fluids into said lumen from the surrounding environment.

8. The infusion catheter or probe of claim 7 wherein said catheter or probe has centering nubs radially extending therefrom and adjacent to the distal end thereof, said centering nubs being positioned to permit unrestricted flow of fluid from said radial openings formed therein.

9. A fluidic infusion system including an in vivo catheter or probe for introducing a select fluid into the environment surrounding a functional end of said catheter or probe, comprising:

a catheter or probe for in vivo placement having a tubulus configuration with at least one axially extending lumen through which fluid is transported from an opening formed by said lumen in a commencing end of said catheter or probe to a closed distal end thereof, and a plurality of circumferentially spaced radial openings formed through the body of said catheter or probe communicating with said fluidic lumen to introduce fluid into the environment surrounding the distal end of the catheter or probe, said radial openings being axially spaced from said distal end by a select spacing, said catheter or probe further including a sensor/electrode proximate the distal end of said catheter or probe to perform a measurement, sensing or stimulation function together with said introduction of fluid into the environment surrounding the distal end of said catheter or probe;

reservoir means for storing said select fluid;

pump means for transporting said fluid with volumetric control through said infusion system, said pump means being responsive to control signals for continuous or selectively intermittent operation and for metering the volume of fluid flowed therethrough;

means for controlling said pump means, said control means having electronic circuitry for generating control signals for and providing control signals to said pump to determine continuous or selectively intermittent operation and to determine the metered volume of fluid flowed thereby;

first fluid conduit means for transporting fluid to said pump means from said reservoir means;

manifold means for introducing fluid into said fluidic lumen of said catheter or probe for transport thereby to the distal end; and second fluid conduit means for transporting fluid to said manifold from said pump means.

10. The fluidic infusion system of claim 9 wherein said radial openings formed in the body of said catheter or probe are each axially spaced the same distance from the distal end thereof.

11. The fluidic infusion system of claim 9 wherein said radial openings formed in the body of said catheter or probe are axially spaced at varying distances from the distal end thereof.

12. The fluidic infusion system of claim 9 wherein said catheter or probe has a plurality of axially extending lumens through which fluid(s) is transported from openings formed by said lumens in a commencing end of said catheter or probe to a closed distal end thereof, each of said lumens communicating with at least one of said plurality of circumferentially spaced radial openings formed through the body of said catheter or probe to introduce said fluid(s) into the environment surrounding the distal end of the catheter or probe.

13. The fluid infusion system of claim 12 additionally comprising a plurality of reservoir means, pump means, and first and second conduit means in cooperating parallel arrangement communicating with at least one each of said fluidic lumens for providing a plurality of select fluids to the environment surrounding the functional end of said catheter or probe.

14. The fluidic infusion system of claim 9 wherein each radial opening formed through the body of said catheter or probe additionally comprises means for preventing reversion flow of fluids into said lumen from the surrounding environment.

15. The fluidic infusion system of claim 14 wherein said catheter or probe has centering nubs radially extending from its body adjacent to the distal end thereof, said centering nubs being positioned to permit unrestricted flow of fluid from said radial openings formed therein.

16. The fluidic infusion system of claim 9 wherein each radial opening formed through the body of said catheter or probe is plugged with a prescribed membrane that only allows molecules less than a prescribed size to pass therethrough.

17. A catheter or probe for in vivo placement having a tubulus configuration with at least one axially extending lumen through which fluid is transported from an opening formed by said lumen in a commencing end of said catheter or probe to a closed distal end thereof, and a sensor for performing a measurement function of the bodily liquids or tissue in which the catheter or probe is implanted, said sensor being embedded in a material which closes the distal end of said catheter or probe and said material having a porous character to fluidically communicate between said fluidic lumen and the environment surrounding the distal end of the catheter or probe to introduce fluid into such surrounding environment.

18. A fluidic infusion system including an in vivo catheter for introducing a select fluid into the environment surrounding a functional end of said catheter, comprising:

a catheter for in vivo placement having a tubulus configuration, said catheter including,
at least one axially extending lumen through which fluid is transported from an opening formed by said lumen in a commencing end of said catheter to a closed distal end thereof,
a plurality of circumferentially spaced radial openings formed through a body of said catheter and communicating with said fluidic lumen to introduce fluid into the environment surrounding the distal end of the catheter, said radial openings being axially spaced from said distal end by a select spacing,
a material which closes the distal end of said catheter; and
a sensor or electrode for performing a measurement, sensing or stimulation function of the bodily liquids or tissue in which the catheter is implanted embedded in the material which closes the distal end of the catheter;

reservoir means for storing said select fluid;

pump means for transporting said fluid with volumetric control through said fluidic infusion system, said pump means being responsive to control signals for continuous or selectively intermittent operation and for metering the volume of fluid flowed therethrough;

means for controlling said pump means, said control means including,
electronic circuitry for generating and providing said control signals to said pump means to determine continuous or selectively intermittent operation and to determine the metered volume of fluid flowed thereby, and
synchronizing means for controlling said pump means to cease fluid flow for a select period during which a measurement, sensing or stimulation function is being performed by a sensor or electrode of said catheter;

first fluid conduit means for transporting fluid to said pump means from said reservoir means;

manifold means for introducing fluid into said fluidic lumen of said catheter for transport thereby to the distal end; and second fluid conduit means for transporting fluid to said manifold means from said pump means.

19. The fluidic infusion system of claim 18 wherein said radial openings formed in the body of said catheter are each axially spaced the same distance from the distal end thereof.

20. The fluidic infusion system of claim 18 wherein said radial openings formed in the body of said catheter are axially spaced at varying distances from the distal end thereof.

21. The fluidic infusion system of claim 18 wherein each radial opening formed through the body of said catheter additionally comprises means for preventing reversion flow of fluids into said lumen from the surrounding environment.

22. The fluidic infusion system of claim 18 wherein said catheter has a plurality of axially extending lumens through which fluid is transported from openings formed by said lumens in a commencing end of said catheter to a closed distal end thereof, each of said lumens communicating with at least one of said plurality of circumferentially spaced radial openings formed through the body of said catheter to introduce said fluid into the environment surrounding the distal end of the catheter.

23. The fluid infusion system of claim 22 additionally comprising a plurality of reservoir means, pump means, and first and second conduit means in cooperating parallel arrangement communicating with at least one each of said fluidic lumens for providing a plurality of select fluids to the environment surrounding the functional end of said catheter.

24. The fluidic infusion system of claim 18 wherein said catheter has centering nubs radially extending from its body adjacent to the distal end thereof, said centering nubs being positioned to permit unrestricted flow of fluid from said radial openings formed therein.

25. The fluidic infusion system of claim 18 wherein each radial opening formed through the body of said catheter is plugged with a prescribed membrane that only allows molecules less than a prescribed size to pass therethrough.

* * * * *